United States Patent [19]

Cox

[11] 4,179,473

[45] Dec. 18, 1979

[54] PRODUCTION OF MONOALKYL AROMATICS

[75] Inventor: Robert P. Cox, Wyckoff, N.J.

[73] Assignee: The Lummus Company, Bloomfield, N.J.

[21] Appl. No.: 950,243

[22] Filed: Oct. 10, 1978

[51] Int. Cl.$^2$ ............................ C07C 3/54; C07C 3/62
[52] U.S. Cl. ................................. 585/313; 585/323 T
[58] Field of Search .......................... 260/671 R, 672 T

[56] References Cited

U.S. PATENT DOCUMENTS

| | | | |
|---|---|---|---|
| 2,747,003 | 5/1956 | Kilpatrick | 260/671 R |
| 2,778,862 | 1/1957 | Gorham et al. | 260/671 R |

Primary Examiner—Delbert E. Gantz
Assistant Examiner—C. E. Spresser
Attorney, Agent, or Firm—Louis E. Marn; Elliot M. Olstein

[57] ABSTRACT

Alkylation of an aromatic is provided in a reactor having a central alkylation zone, and a surrounding transalkylation zone. The reaction mixture flows cocurrently through the alkylation zone and then into the surrounding transalkylation zone, with the mixture flowing in approximate plug flow through the transalkylation zone to the outlet thereof. Polyalkyl aromatics recovered from the effluent are recycled to the inlet end of the transalkylation zone.

5 Claims, 1 Drawing Figure

U.S. Patent    Dec. 18, 1979    4,179,473
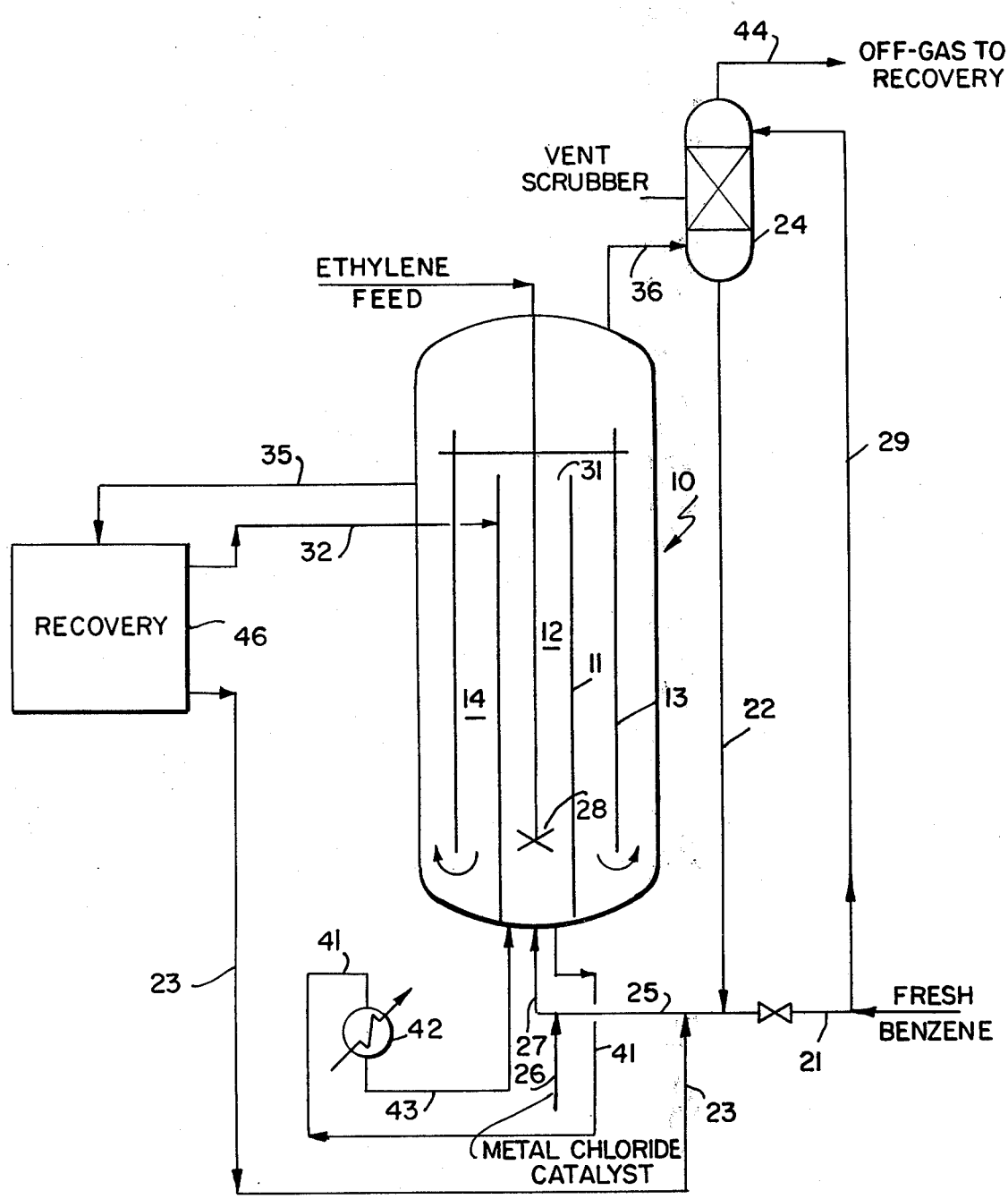

PRODUCTION OF MONOALKYL AROMATICS

This invention relates to the production of monoalkyl aromatics, and more particularly to a new and improved process for the production of monoalkyl aromatics by reaction between an olefin and an aromatic compound.

In the production of an alkyl aromatic by reaction of aromatic with olefin; e.g., ethylbenzene by reaction between benzene and ethylene, ethylene and benzene are introduced into a back-mix vessel, with reaction liquid being pumped through an external heat exchanger to remove reaction heat. The alkylation effluent is then introduced into a second reactor to effect transalkylation of polyethylated benzenes to ethyl benzene.

The present invention is directed to an improvement in the overall process for producing monoalkyl aromatics by reaction of olefin and aromatic compound.

In accordance with the present invention, there is provided a combination alkylation-transalkylation reactor comprised of a central alkylation zone, and a surrounding transalkylation zone, with the aromatic, olefin, metal chloride alkylation catalyst and hydrogen cloride being introduced into an inlet end of the alkylation zone and being caused to cocurrently flow therethrough at alkylation conditions, and thereafter to flow through the surrounding transalkylation zone in essentially plug flow to the outlet of such transalkylation zone. Polyalkyl aromatics recovered from the effluent withdrawn from the transalkylation zone are recycled to the inlet end of the transalkylation zone to effect conversion thereof to monoalkyl aromatic by transalkylation with aromatics present in the alkylation zone effluent. The polyalkyl aromatic may be recycled to the transalkylation without preheating thereof.

The alkylation and transalkylation are generally effected at a temperature of from 225° F. to 425° F., and at a pressure in the order of from 75 to 600 psig. In general, the ratio of aromatic compound to olefin is in the order of from 1:1 to 5:1. The conditions for effecting such alkylation and transalkylation are generally known in the art, and no further details in this respect are deemed necessary for a complete understanding of the present invention.

The aromatic feed is generally preferably benzene. The olefin is preferably a gaseous olefin; such as, propylene or ethylene, with ethylene being preferred. It is to be understood, however, that the olefin could be one which is normally liquid. As should be apparent, the olefin is selected to provide the desired alkyl group on the aromatic compound.

The invention will be further described with respect to the accompanying drawing, wherein:

The drawing is a simplified schematic flow diagram of an embodiment of the present invention.

The embodiment will be particularly described with respect to the production of ethyl benzene from benzene and ethylene; however, the scope of the invention is not limited to such production.

Referring to the drawing, there is shown a vertical reactor 10 provided with a vertical cylindrical baffle 11, connected to the bottom of reactor 10 and spaced from the top thereof, with baffle 11 defining a central axial alkylation zone 12. The reactor 10 is further provided with a cylindrical baffle 13 which surrounds baffle 11, with baffle 13 being spaced from the top and bottom of reactor 10. The portion of reactor 10 outside of baffle 11 defines a transalkylation zone 14, with baffle 13 being employed to provide for essentially plug flow within the transalkylation zone 14. The baffle 13 could be eliminated or additional baffles can be added depending on the economics of providing an approach to plug flow in transalkylation zone 14. Although the baffle 13 is in the form of a cylindrical baffle it is to be understood that other configurations, such as, spirals, discs, etc., which provide for plug flow are also possible.

The baffle 11 and reactor 10, as well as the processing conditions, are selected such that essentially all of the ethylene is reacted prior to fluid passage from the alkylation zone 12 to the transalkylation zone 14. Thus, the liquid which passes over baffle 11 into the transalkylation zone 14 is essentially free of ethylene.

Fresh feed benezene in line 21 is combined with benzene containing absorbed hydrogen chloride in lines 22 and 23, obtained from a vent scrubber 24 and a flash scrubber (not shown) respectively, obtained as hereinafter described. The combined stream in line 25 is further combined with metal chloride catalyst; in particular, aluminum chloride, and makeup hydrogen chloride, in line 26 to form a homogeneous mixture in line 27 which is introduced into the inlet end of the alkylation zone 12. Fresh feed ethylene is introduced into the inlet end of alkylation zone 12 through a sparger 28. The combined stream flows cocurrently upwardly through the alkylation zone 12, with such alkylation zone being operated at alkylation conditions in order to produce ethyl and polyethyl substituted benzene.

The exothermic heat of reaction is removed from zone 12 by circulating a portion of the liquid through a separate cooling loop, including line 11, cooler 42 and line 43.

At the outlet end 31 of alkylation zone 12 essentially all of the ethylene has been reacted to produce mono and polyethyl benzenes. At the outlet end 31, recycle polyethyl benzene in line 32 is added to the reaction mixture which overflows baffle 11 into the transalkylation zone 14 wherein the polyethyl benzenes reacts with benzene to produce monoethyl benzene.

The mixture flows downwardly between baffles 11 and 13, and then upwardly between baffle 13 and the wall of reactor 10 to an outlet 35. It is to be understood that other flow paths are possible as long as plug flow is approached.

Gas is vented from reactor 10 through line 36, and such vent gas contains vaporized benzene and hydrogen chloride, and may further include any hydrogen or alkane, such as methane or ethane, introduced with the ethylene.

In the embodiment shown, vent gas in line 36 is introduced into a vent scrubber 24 wherein the gas is contacted with fresh feed benzene in line 29 to absorb any remaining hydrogen chloride and benzene. The gas withdrawn from vent scrubber 24 through line 44 may be further treated to recover additional components and to neutralize any hydrogen chloride. The fresh feed benzene, containing absorbed components, withdrawn from scrubber 24 through line 22 is eventually recycled to the alkylation zone 12, as hereinabove described.

The reaction effluent withdrawn from reactor 10 through line 35 is introduced into a separation and recovery zone, schematically generally indicated as 46. The separation and recovery zone 46 may include a product flash zone wherein the liquid reaction product is flashed, while hot, to reduce the amount of dissolved hydrogen chloride. Vapor, containing hydrogen chloride, as well as some benzene and alkyl benzene, which is flashed from the effluent, may be introduced into a condenser to effect condensation of all of the ethylbenzene, with such condensation also resulting in condensation of a major portion of the benzene. The remaining gas may be further scrubbed with fresh feed benzene to recover hydrogen chloride, with such benzene, containing absorbed hydrogen chloride being eventually passed to the alkylation zone 12 through line 23, as hereinabove described.

The recovery zone 46 also includes means for effecting separation of polyethyl benzenes from ethylbenzene, with such polyethyl benzenes being recycled, without heating thereof, for transalkylation, as hereinabove described.

Although the invention has been particularly described with respect to the embodiment illustrated in the accompanying drawing, it is to be understood that the invention may be practiced otherwise than as described with respect to such drawing. Thus, for example, the alkylation reactor may be operated with the use of a reflux condenser instead of an external cooling loop.

These and other modifications should be apparent to those skilled in the art from the teachings herein.

The present invention is particularly advantageous in that by providing for plug flow in the transalkylation zone, the volume of the zone may be reduced and/or the reaction may proceed to a greater extent. In addition costs are reduced by providing a single reactor for both reactions. Furthermore, heating of polyalkyl aromatics recycle is eliminated. Moreover, the geometry of the alkylation zone is improved which reduces side reactions. These advantages and others should be apparent from the teachings herein.

Numerous modifications and variations of the present invention are possible in light of the above teachings and, therefore, within the scope of the appended claims, the invention may be practiced otherwise than as particularly described.

I claim:

1. A process for producing a monoalkyl aromatic by reaction between olefin and aromatic, comprising:
   introducing aromatic, olefin and alkylation catalyst into a combination alkylation-transalkylation reactor comprised of a central alkylation zone and a surrounding transalkylation zone, said aromatic and olefin being introduced into said alkylation zone and caused to flow cocurrently therethrough at alkyl aromatic production conditions to produce monoalkyl aromatic product and polyalkyl aromatic by-product, and then in plug flow through said surrounding transalkylation zone to effect transalkylation to monoalkyl aromatic;
   withdrawing an effluent from the transalkylation zone containing monoalkyl aromatic product and polyalkyl aromatic by-product;
   recovering monoalkyl aromatic product and polyalkyl aromatic by-product from the effluent; and
   introducing polyalkyl aromatic by-product into the inlet portion of the transalkylation zone.

2. The process of claim 1 wherein the polyalkyl aromatic is recycled without preheating thereof.

3. The process of claim 2 wherein the alkylation and transalkylation zones are operated at a temperature of from 225° to 425° F. and a pressure of from 75 to 600 psig.

4. The process of claim 2 wherein the aromatic is benzene and the olefin is ethylene.

5. The process of claim 4 wherein the catalyst is aluminum chloride.

* * * * *